(12) United States Patent
Sharratt (10) Patent No.: US 6,663,563 B1
(45) Date of Patent: Dec. 16, 2003

(54) FASTENING SYSTEM FOR RETRACTOR SUPPORT

(75) Inventor: Todd W. Sharratt, Cottage Grove, MN (US)

(73) Assignee: Minnesota Scientific, Inc., St. Paul, MN (US)

( * ) Notice: Subject to any disclaimer, the term of this patent is extended or adjusted under 35 U.S.C. 154(b) by 23 days.

(21) Appl. No.: 09/624,950

(22) Filed: Jul. 25, 2000

Related U.S. Application Data

(63) Continuation-in-part of application No. 09/409,294, filed on Sep. 29, 1999, now Pat. No. 6,210,325.
(60) Provisional application No. 60/102,788, filed on Oct. 2, 1998.

(51) Int. Cl.[7] .................................................. A61B 1/32
(52) U.S. Cl. .................... 600/228; 600/229; 600/227
(58) Field of Search ................................ 600/213, 227, 600/228, 229, 230, 234, 184

(56) References Cited

U.S. PATENT DOCUMENTS

| | | | |
|---|---|---|---|
| 2,893,378 A | 7/1959 | Cooper | |
| 3,858,578 A | 1/1975 | Milo | |
| 4,143,652 A | 3/1979 | Meier et al. | |
| 4,867,404 A | * 9/1989 | Harrington et al. | 248/231.4 |
| 5,284,130 A | * 2/1994 | Ratliff | |
| 5,400,772 A | 3/1995 | LeVahn et al. | |
| 5,513,827 A | * 5/1996 | Michelson | 248/279.1 |
| 6,210,325 B1 | * 4/2001 | Bartie et al. | 600/229 |

* cited by examiner

Primary Examiner—Jeffrey A. Smith
(74) Attorney, Agent, or Firm—Westman, Champlin & Kelly, P.A.

(57) ABSTRACT

A fastening mechanism of the present invention includes a docking unit partially disposed within a housing, the fastening mechanism capable of securing a docking pin attached to a retractor. The fastening mechanism is attached to a positioning arm and is capable of engaging the docking pin regardless of the position of the positioning arm.

14 Claims, 11 Drawing Sheets

FASTENING SYSTEM FOR RETRACTOR SUPPORT

This is a continuation-in-part application of application Ser. No. 09/409,294 filed Sep. 29, 1999, now U.S. Pat. No. 6,210,325 B1, which is a provisional of application Ser. No. 60/102,788 filed Oct. 2, 1998.

BACKGROUND OF THE INVENTION

The present invention generally relates to a retractor system that is useful in surgical procedures. More specifically, the present invention relates to a surgical support structure, such as a retractor apparatus, and to a clamping mechanism for a retractor system. The present invention further relates to illuminating a retractor apparatus.

During many types of surgical procedures, such as micro endoscopic and direct division discectomy, it is customary to use a retractor. The retractor is used to hold back tissue proximate a surgical incision to enable a surgeon to work at and in the surgical incision. Retractors typically include a blade and an arm, such as a shaft, to which the blade is attached. The retractor is generally held in place by attachment to a retractor support apparatus that is positioned over a support surface, such as an operating table. The retractor support is usually attached to a side rail located along one or more sides of the operating table by a clamping device, such as a fulcrum clamp or a cammed clamp.

During surgical procedures, it is highly desirable that the retractor be flexible in order to precisely position the retractor. Quickly securing the retractor in the desired position is also equally important in promoting efficient and safe surgical procedures. Simple horizontal and vertical adjustment of the retractor at the clamping device positioned along the sides of the operating table are also key requirements for successful surgical procedures.

Current retractors are not easy to manipulate and position over the surgical incision since the arm is typically a solid inflexible rod. Locking mechanisms to lock the retractors in a precise location are typically cumbersome and require complex maneuvers that may increase the risk of injury to the patient. Horizontal and vertical adjustment of the retractor at the clamping device that attaches the retractor to the sides of the operating table still remains challenging since the clamping device may be difficult to operate, or be located at a place that may increase the risk of contamination to the patient. Thus, an urgent need presently exists to produce a retractor that overcomes these challenges.

SUMMARY OF THE INVENTION

The present invention includes a fastening system for securing a retractor to a retractor support arm, the fastening system including a docking pin that is attached to the retractor. The fastening mechanism is attached to the retractor support arm and frictionally secures the docking pin when engaging the docking pin.

DETAILED DESCRIPTION

Figure 1:
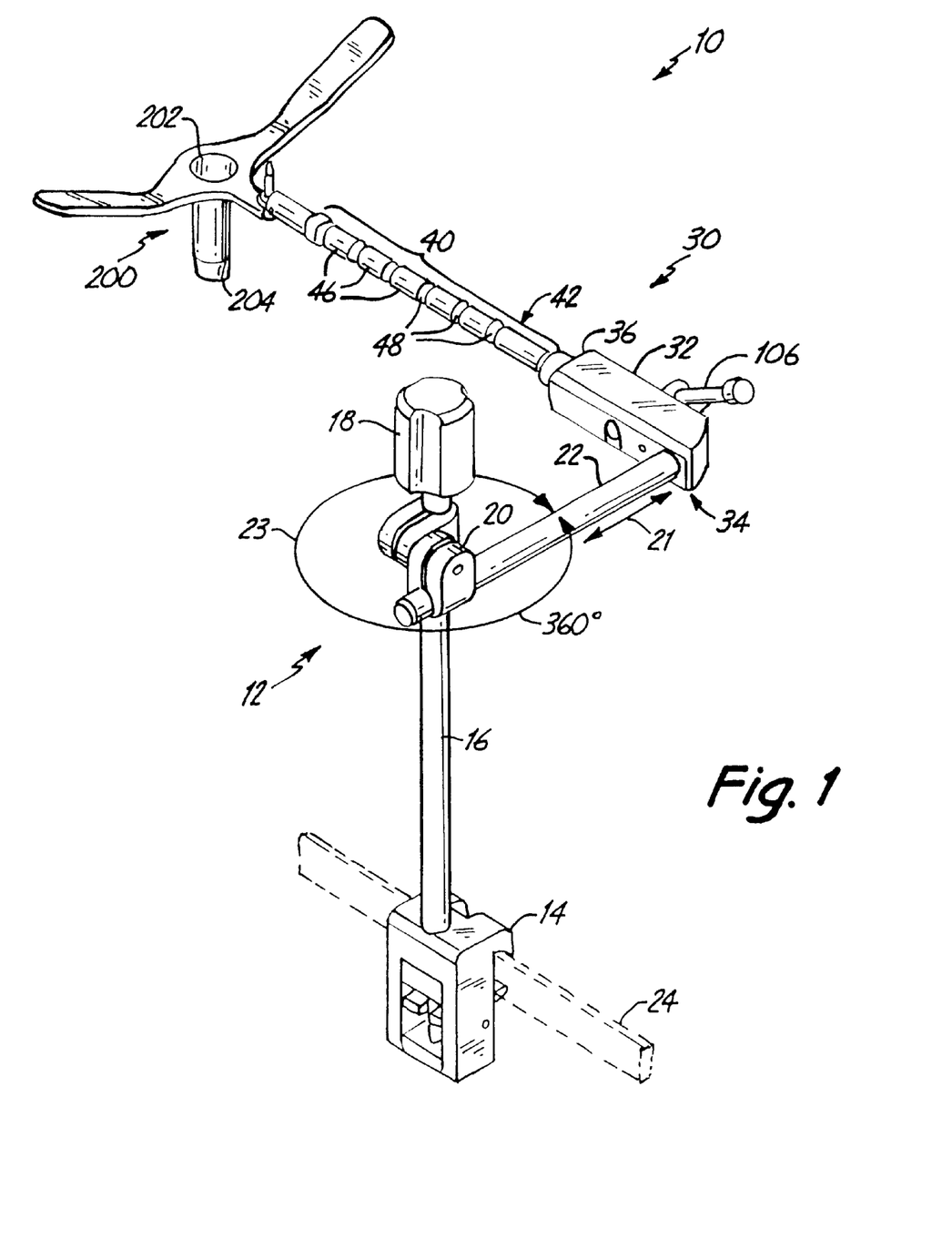
FIG. 1 is a perspective view of a surgical retractor apparatus of the present invention.

A retractor system of the present invention is generally depicted at 10 in FIG. 1. The retractor system 10 includes a clamping system 12 and a retractor apparatus 30. The clamping system 12 includes a support clamp 14, a clamp support rod 16, a clamp knob 18, a retractor clamp 20, and a retractor support rod 22. A suitable clamping system 12, assigned to the same assignee as the present invention, is described in U.S. Pat. No. 5,400,772 and is incorporated herein by reference. The clamping system 12 adjustably secures the retractor apparatus 30 to the clamp support rod 16 through retractor clamp 20, as best depicted in FIG. 1. The support clamp 14 clamps to a support surface, such as a rail 24 of an operating table (not shown). Turning the clamp knob 18 releases the support clamp 14 and allows the clamping system 12 to move in a horizontal direction along the rail 24. Vertical adjustment of the clamping system 12 is accomplished by releasing the retractor clamp 20 and sliding the retractor clamp 20 adjustably secured to the retractor support rod 22 to a different vertical position. Horizontal adjustment of the retractor apparatus 30 occurs by releasing the retractor clamp 20 secured to the retractor support rod 22 and moving the retractor support rod 22 in direction 21 if desired. Releasing the retractor clamp 20 also permits the retractor apparatus 30 to freely rotate 360° if desired, as indicated by arrow 23.

The retractor apparatus 30 includes a cam-activated device 32, and an adjustable arm 40, as illustrated in FIG. 1. The cam-activated device 32 locks the adjustable arm 40 in a selected position. The cam-activated device 32 has a clamp support portion 34 and a distal end 36 as best depicted in FIG. 1. The clamp support portion 34 has an aperture (not shown) to receive the retractor support rod 22 to attach the clamping system 12 to the retractor apparatus 30. The distal end 36 receives a proximal end 42 of the adjustable arm 40.

Figure 2:
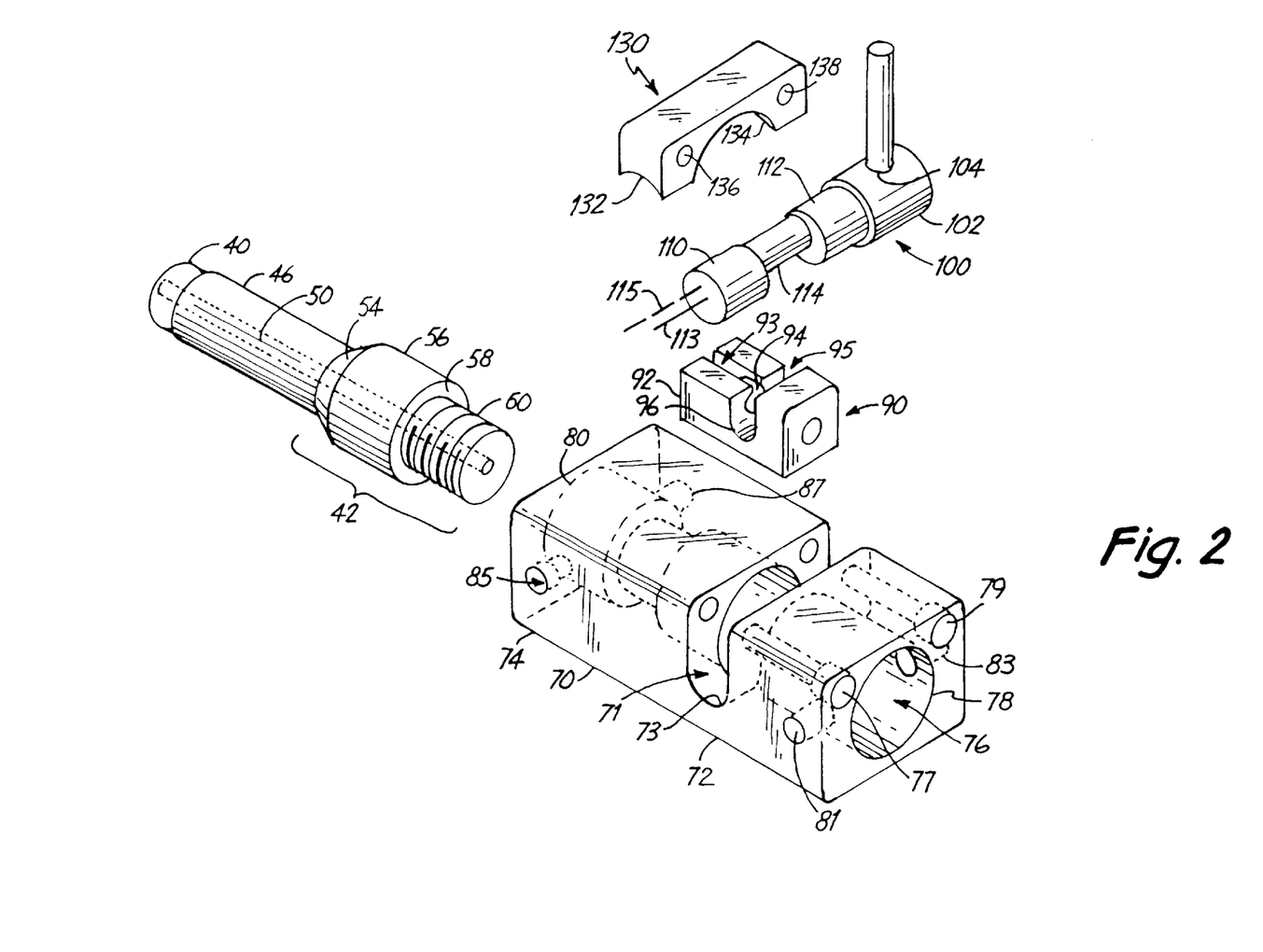
FIG. 2 is an exploded view of an adjustable arm and a cam-activated device of the present invention.
Figure 3:
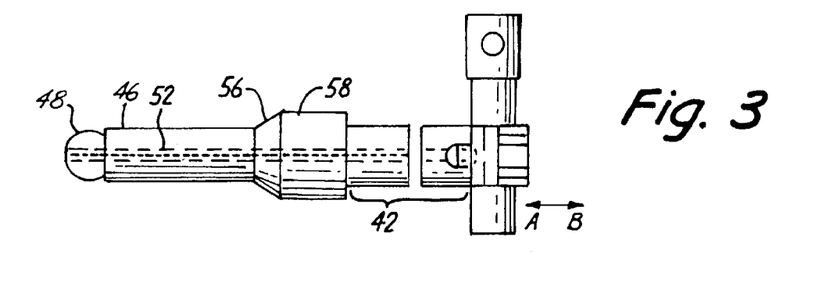
FIG. 3 is a top plan view of the adjustable arm and cam-activated locking device depicted in FIG. 2.
Figure 5:
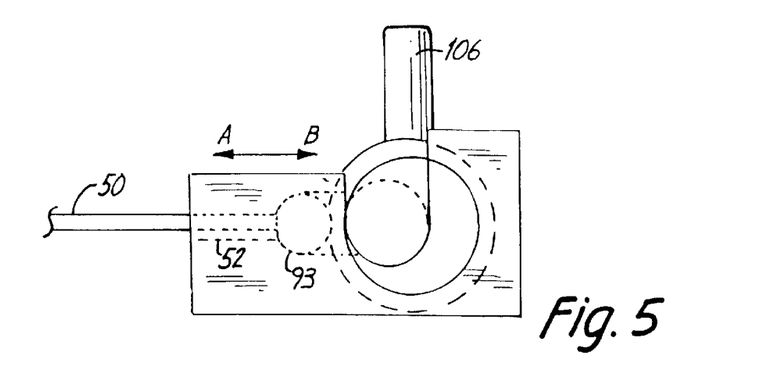
FIG. 5 is a side plan view of the cam-activated locking device depicted in FIG. 3 with portions shown in broken lines for clarity.

The adjustable arm 40, as illustrated in FIGS. 1 and 2, is constructed of alternating cylinder(s) 46 and adjacent sphere(s) 48, connected to each other by a cable 50 extending centrally therethrough. The cable 50 is housed in a bore 52 that extends through each cylinder 46 and adjacent sphere 48 as depicted in FIGS. 3 and 5. The alternating cylinder(s) 46 and adjacent sphere(s) 48 form the adjustable arm 40 that is highly flexible and is easy to manipulate in any direction by the surgeon. Preferably, each cylinder 46 and adjacent sphere 48 are integral with each other being machined from a single piece of metal.

Although alternating cylinders 46 and spheres 48 are used to practice the present invention, any pieced shape may be used to construct the adjustable arm 40, such as barrels, buckets, or the like. Other forms of pieced shapes may be chosen based upon the need to impart more or less flexibility to the adjustable arm 40.

The cam-activated device 32, as best depicted in FIG. 2, includes a housing 70, and a bore 76 that extends centrally through the housing 70. The housing 70 has a proximal portion 72 and a distal portion 74. Likewise, the centrally located bore 76 has a proximal end 78 and a distal end 80.

A frustro-conical surface 54 integral to a cylindrical surface 56 extends above an externally threaded portion 60 of the adjustable arm 40 to form an annular shoulder 58. An internally threaded section (not shown) at the distal end 80 of the bore 76 threadably engages the externally threaded portion 60 of the adjustable arm 40 to securely fix the adjustable arm 40 to the housing 70.

The retractor apparatus 30 further includes a carriage 90 that engages a camming structure 100 for causing a camming action. The carriage is disposed within the proximal end 78 of the bore 76 and extends into a slot 71 of the housing 70. The carriage 90 prevents the camming structure 100 from moving when disposed in slot 71.

The carriage 90 has a groove 93 disposed on a distal end 92 for receiving the cable 50. The cable 50 is attached to a spherical ball 98, as illustrated in FIGS. 3 and 5. The spherical ball 98 is fixedly attached to a spherical groove 94 illustrated in FIG. 2. The spherical groove has a surface conforming to the surface of the spherical ball 98. Therefore, the spherical ball 98 attaches the cable 50 to the carriage 90 as best depicted in FIG. 5. The groove 93 is substantially perpendicular to a cam slot 95 that has a lower semi-cylindrical surface 96 that engages the camming structure 100.

The camming structure 100 has a cylindrical handle section 102 that includes a cam handle bore 104 for engaging a cam handle 106, and two cylindrical sections 110 and 112 of equal diameter disposed on an axis 113. The two cylindrical sections 110 and 112 are preferably oriented substantially perpendicular to the cam handle 106 as illustrated in FIG. 2. The cylindrical section 112 is proximate to the cylindrical handle section 102. The cylindrical sections 110 and 112 engages the cam slot 95 and prevents the cam structure 100 from moving independently of the carriage 90. The cylindrical section 112 is proximate to the cylindrical handle section 102.

Figure 4:
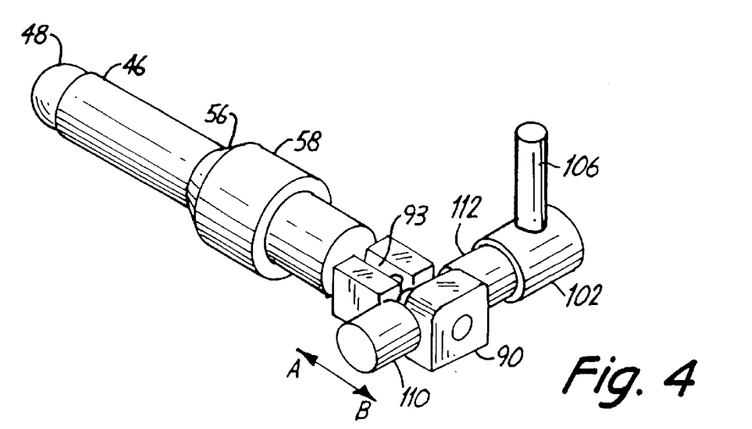
FIG. 4 is a perspective view of the adjustable arm and the cam-activated locking device depicted in FIG. 3.

The camming action is provided by a cam section 114 preferably at an intermediate location between the cylindrical sections 110 and 112. The cam section 114 is smaller in diameter than the cylindrical sections 110 and 112. The cam section 114 has a cam axis 115 that is offset from the cylindrical axis 113. When the cam handle 106 on the cylindrical handle section 102 is rotated about the axis 113, the cam section 114 engages the cam slot 95 and thereby moves the carriage 90 in either direction A or in direction B, as best depicted in FIGS. 3, 4, and 5. When the carriage 90 is moved in either direction A or in direction B, the spherical ball 98 attached to the cable 50 is also moved in direction A or in direction B and thereby releases or stiffens the cable 50 in the adjustable arm 40.

The camming structure 100 also engages the slot 71 in the housing 70. The slot 71 has lower semi-cylindrical bottom surfaces 73 and 75 (not shown) that accepts cylindrical sections 110 and 112, respectively.

A cap 130 fits into slot 71 of the housing 70. The cap 130 secures the camming structure 100 in slot 71 while permitting the camming structure 100 to rotate about axis 113. The cap 130 engages cylindrical sections 110 and 112 with arcuate downwardly facing surfaces 132 and 134, respectively. When the cap 130 is positioned within slot 71, apertures 136 and 138 are aligned with apertures 77 and 79, respectively. Cap screws (not shown) are inserted into apertures 77 and 79 and extend into apertures 136 and 138 of the cap 130. The cap 130 also prevents the camming structure 100 from moving upward and downward when disposed in slot 71.

The housing 70 further includes coaxially disposed apertures 81, 83, 85 and 87. Apertures 81 and 83 are located at the proximal portion 72 of the housing 70. Apertures 85 and 87 are positioned at the distal portion 74 of the housing 70. Apertures 81 and 85 are internally threaded (not shown) to accept set screws (not shown) that extend into the apertures 83 and 87 past the bore 76. The set screws (not shown) that are threadably inserted into apertures 81, 83, 85 and 87 may be used to engage a mounting rail (not shown) to secure the retractor apparatus 30 to a support surface (not shown).

Set screws (not shown) that are threadably inserted into apertures 85 and 87 engage the externally threaded portion 60 of the adjustable arm 40. The externally threaded portion 60 may be turned to decrease or increase the tension in the cable 50 with respect to the carriage 90. This feature is important since the appropriate tension in the cable 50 must be maintained so that when the carriage 90 is moved in direction A or in direction B, the cylinders 46 and adjacent spheres 48 are selectively placed in a relaxed or locked position. The set screws (not shown) that are threadably inserted into apertures 85 and 87 engage the externally threaded portion 60 to lock the externally threaded portion 60 in a selected position in the housing 70 and at a selected distance from the carriage 90.

Abutting an opposite end of the adjustable arm 40 is a fastening system 140. The fastening mechanism 140 is a mechanical system capable of engaging a docking pin 142 attached to the tubular retractor 200 as illustrated in FIG. 1. The fastening mechanism 140 includes a docking unit 160, and a spring 148, disposed within a cylindrical housing unit 150 as illustrated in FIGS. 8 through 11. The fastening mechanism 140 abuts against the adjustable arm 40, and is secured by the cable 50, the cable 50 urging the unit 160 deeper within the housing unit 150.

Figure 12:
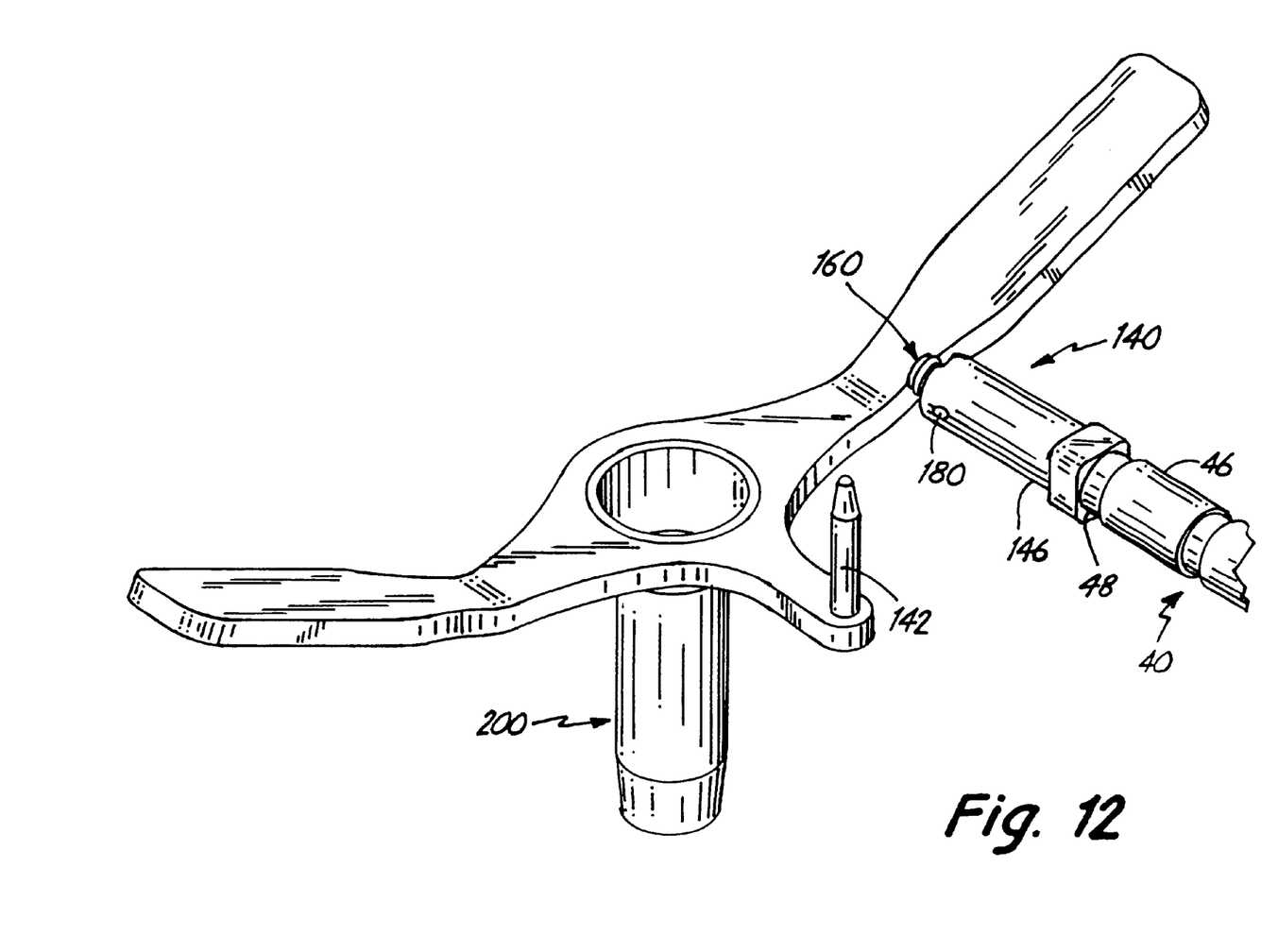
FIG. 12 is a perspective view of the fastening device of the present invention.

When the adjustable arm 40 is in the relaxed state, the fastening mechanism 140 is freely rotatable, thus allowing the surgeon to position the adjustable arm 40 and the fastening mechanism 140 such that a docking aperture 152 aligns with the docking pin 142 as illustrated in FIG. 12. Once the fastening system 140 has engaged the docking pin 142, the retractor apparatus 30 is activated, drawing the docking unit 160 deeper within the cylindrical housing unit 150, and frictionally securing the docking pin 142 into place.

Figure 8:
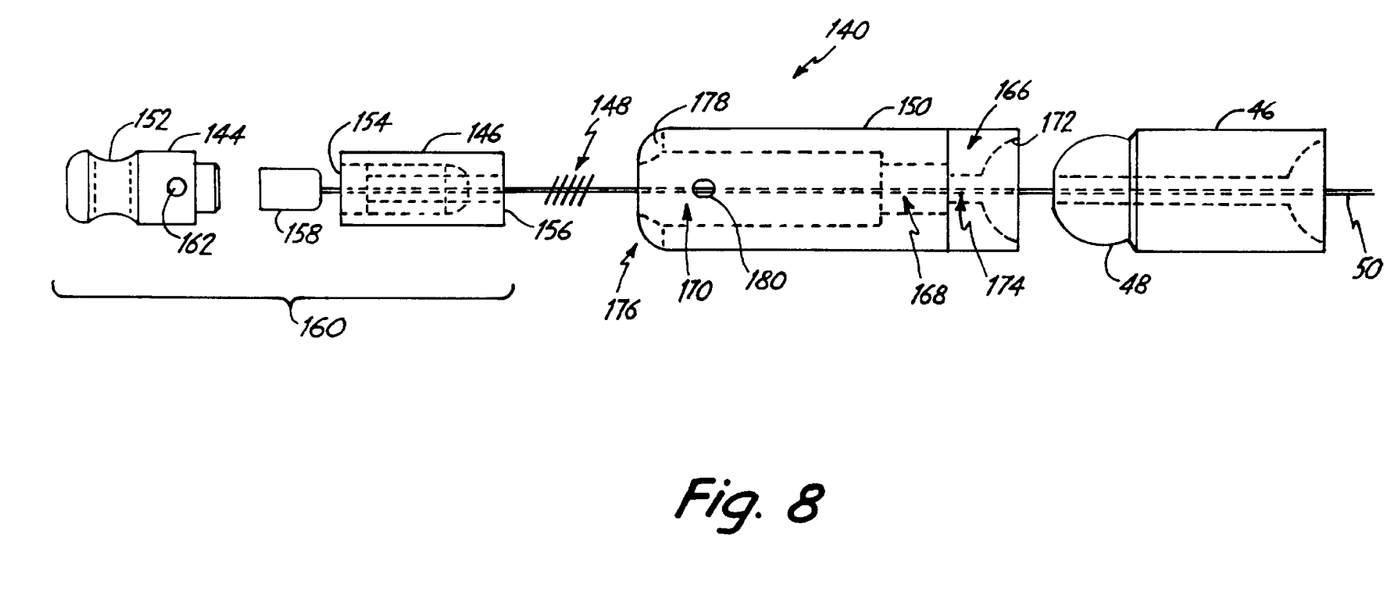
FIG. 8 is an exploded plan view of a fastening system of the present invention.

The docking unit 160 includes a docking piece 144 and a hollow cylindrical spacer 146. The hollow cylindrical spacer 146 includes a receiving end 154 and a stopping end 156, as illustrated in FIG. 8. The inside diameter of the receiving end 154 is great enough so as to allow a cylindrical nub 158, attached to the cable 50, to nest within the spacer 146. The inside diameter of the stopping end 156 does not allow passage of the nub 158, the inside diameter of the stopping end 156 being only slightly larger than the diameter of the cable 50.

Figure 10:
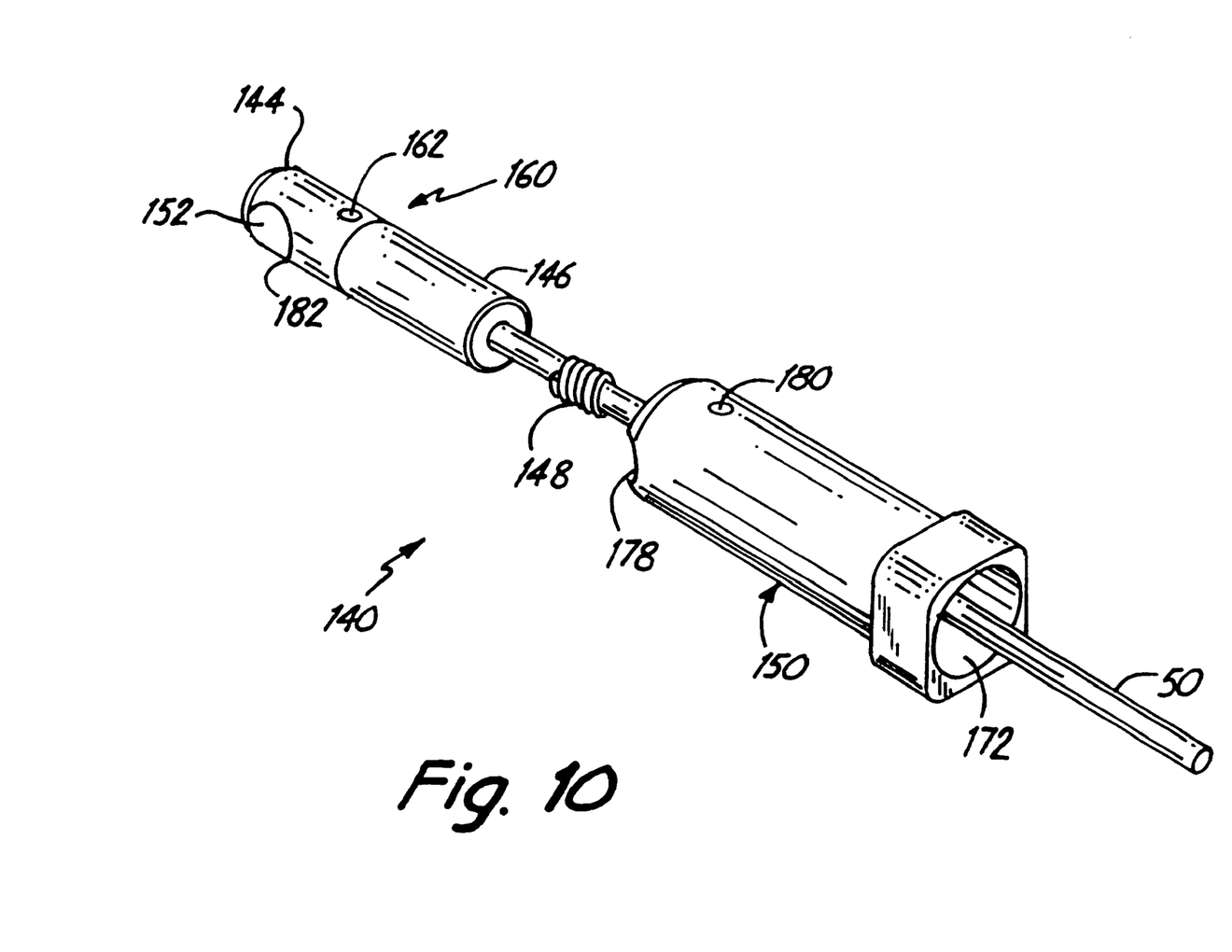
FIG. 10 is a perspective view of the fastening device of the present invention.

With the nub 158 nested within the spacer 146, the receiving end 154 is fixedly attached to the docking piece 144, as illustrated in FIG. 10. The docking piece 144 has substantially the same outer diameter of the spacer 146, and once fixedly attached to each other, the docking piece 144 and the spacer 146 essentially form the docking unit 160. In the preferred embodiment, the docking piece 144 and the spacer 146 are brazened to one another to form the unit 160. This unit 160 is freely rotatable with respect to the nub 158 and cable 50.

Figure 9:
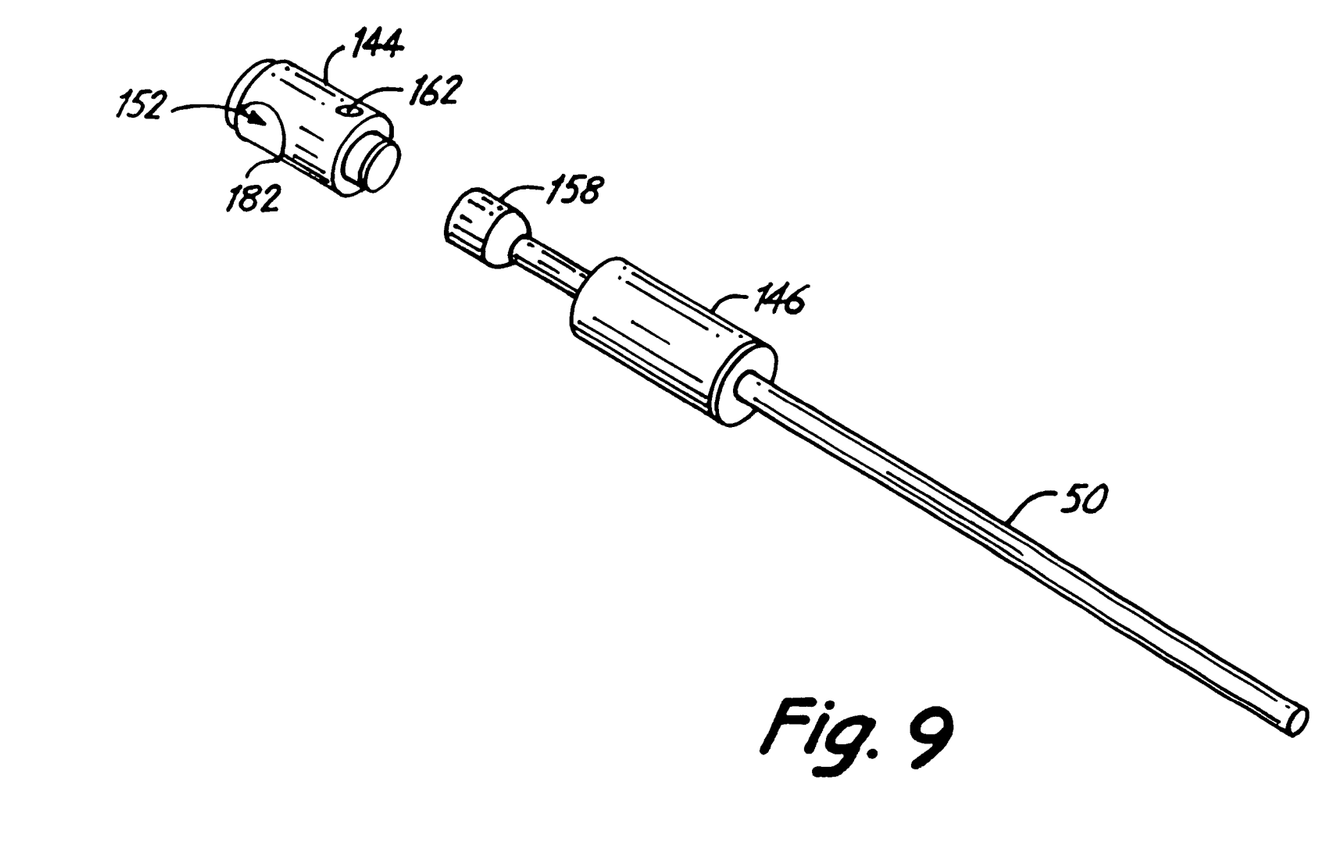
FIG. 9 is a perspective view of a docking unit and cable of the present invention.

The docking end 144 of the unit 160 includes the docking aperture 152 and a cotter pin hole 162, as illustrated in FIG. 9. The docking aperture 152 is capable of engaging the docking pin 142, and thus has a diameter only slightly larger than the docking pin 142. The cotter pin hole 162 is located on an axis perpendicular to the docking aperture 152 and accommodates a cotter pin 164. The cotter pin 164 controls the horizontal and rotational movement of the cylindrical housing unit 150, as will be described.

Figure 11:
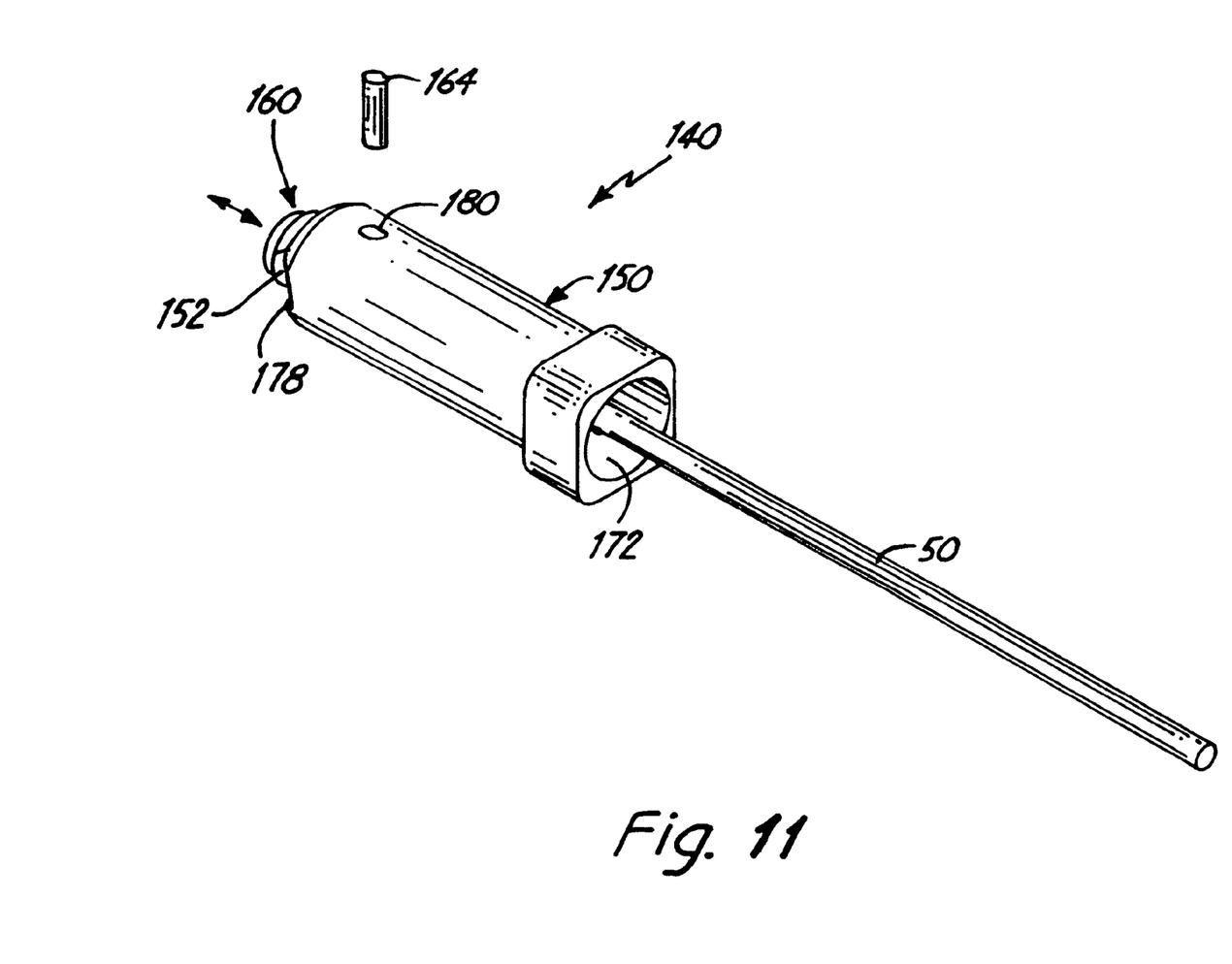
FIG. 11 is a perspective view of the fastening device of the present invention.

The docking unit 160 further includes an outside diameter such that the unit 160 is capable of partially nesting within the cylindrical housing 150, as illustrated by FIG. 11. The cylindrical housing 150 includes an abutting portion 166, a spring cavity 168, and a nesting portion 170 (FIG. 8). The abutting portion 166 has a hemispherical indentation 172 capable of partially engaging the adjacent sphere 48 of the adjustable arm 40, and includes an aperture 174 therethrough in which the cable 50 travels.

The spring cavity 168 houses the spring 148 which acts upon the abutting portion 166 and the spacer 146 of the docking unit 160, urging the docking unit 160 out of the housing unit 150. The force that the spring 148 exerts upon the unit 160 is great enough to counteract an opposing force of the cable 50 when the adjustable arm 40 is in the relaxed state. This allows the docking aperture 152 of the docking piece 144 to be freely accessible to cooperate with the docking pin 142, while the adjustable arm 40 is in the relaxed state. It should be appreciated that while in the relaxed state, the adjustable arm 40 may be flexed in virtually any direction or position without the force of the cable 50 overcoming the force of the spring 148. Thus, while flexing the adjustable arm 40, the docking unit 160 is not allowed to be drawn deeper within the cylindrical housing 150. This allows the docking pin 142 to be inserted through the docking aperture 152 regardless of the position of the adjustable arm 40.

Figure 13:
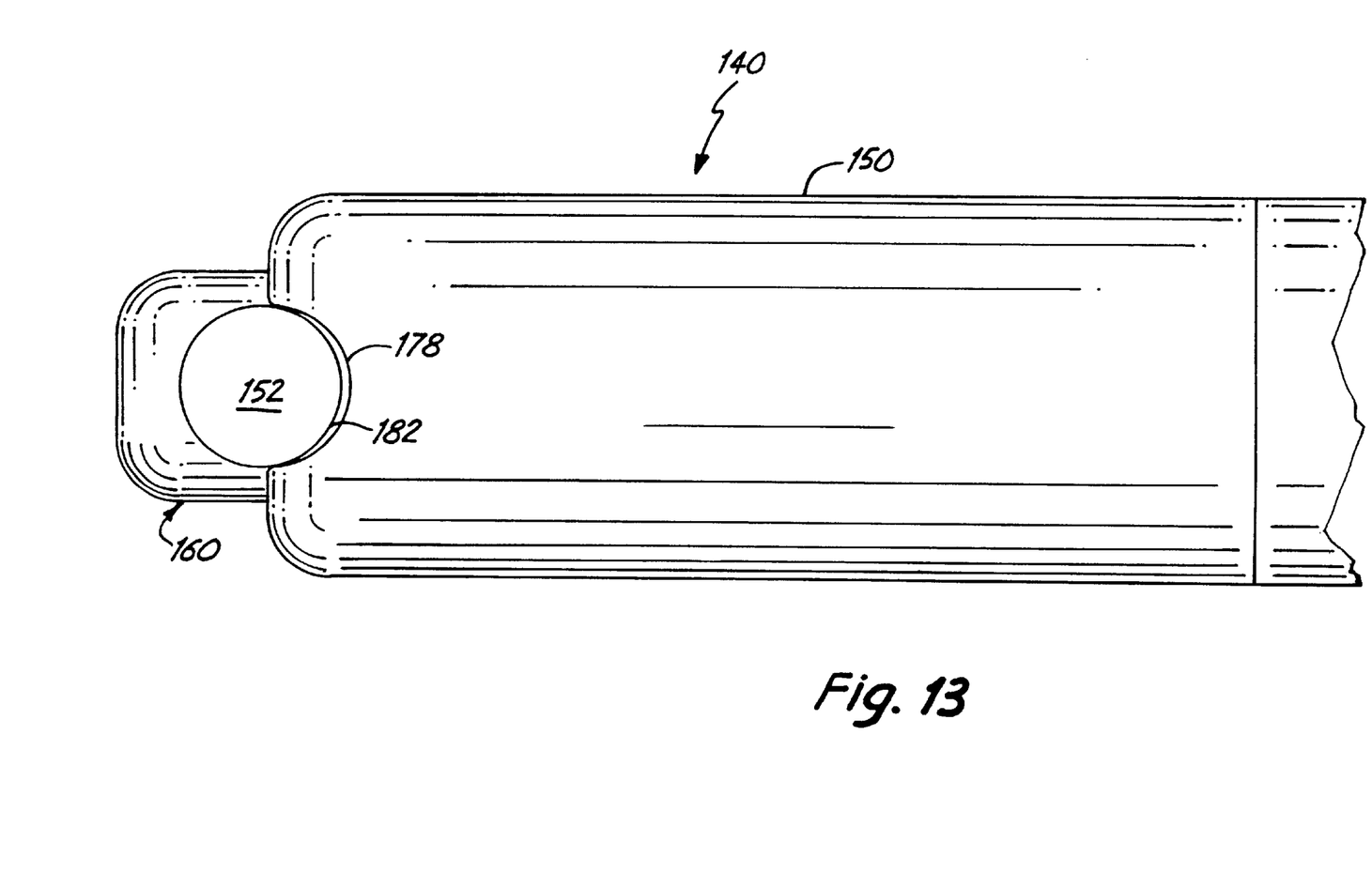
FIG. 13 is a side view of a docking aperture being substantially aligned with an indentation of a housing unit of the present invention.

A distal end 176 of the cylindrical housing 150 contains two semicircular indentations 178. The indentations 178 coincide with the docking aperture 152 of the docking unit 160 once the unit 160 has been partially inserted within the cylindrical housing 150 as illustrated in FIG. 13. The indentations 178 are kept aligned with the docking aperture 152 by two slotted apertures 180 (FIG. 11) positioned through the cylindrical housing 150 so as to cooperate with the cotter pin hole 162 of the docking unit 160. As FIG. 11 illustrates, the slotted apertures 180 are elongated in a direction which permits slight horizontal travel of the docking unit 160 within or out of the housing unit 150, but does not permit any rotational movement of the housing unit 150 with respect to the docking unit 160. It should be understood, though that the fastening mechanism 140 itself is still free to rotate. Thus once the cotter pin 164 has been inserted through the cotter pin hole 162 and the slotted apertures 180, the docking unit 160 is allowed to travel slightly within or out of the cylindrical housing 150, as indicated by the arrows in FIG. 11, approximately a distance equal to the length of the slotted apertures.

Figure 14:
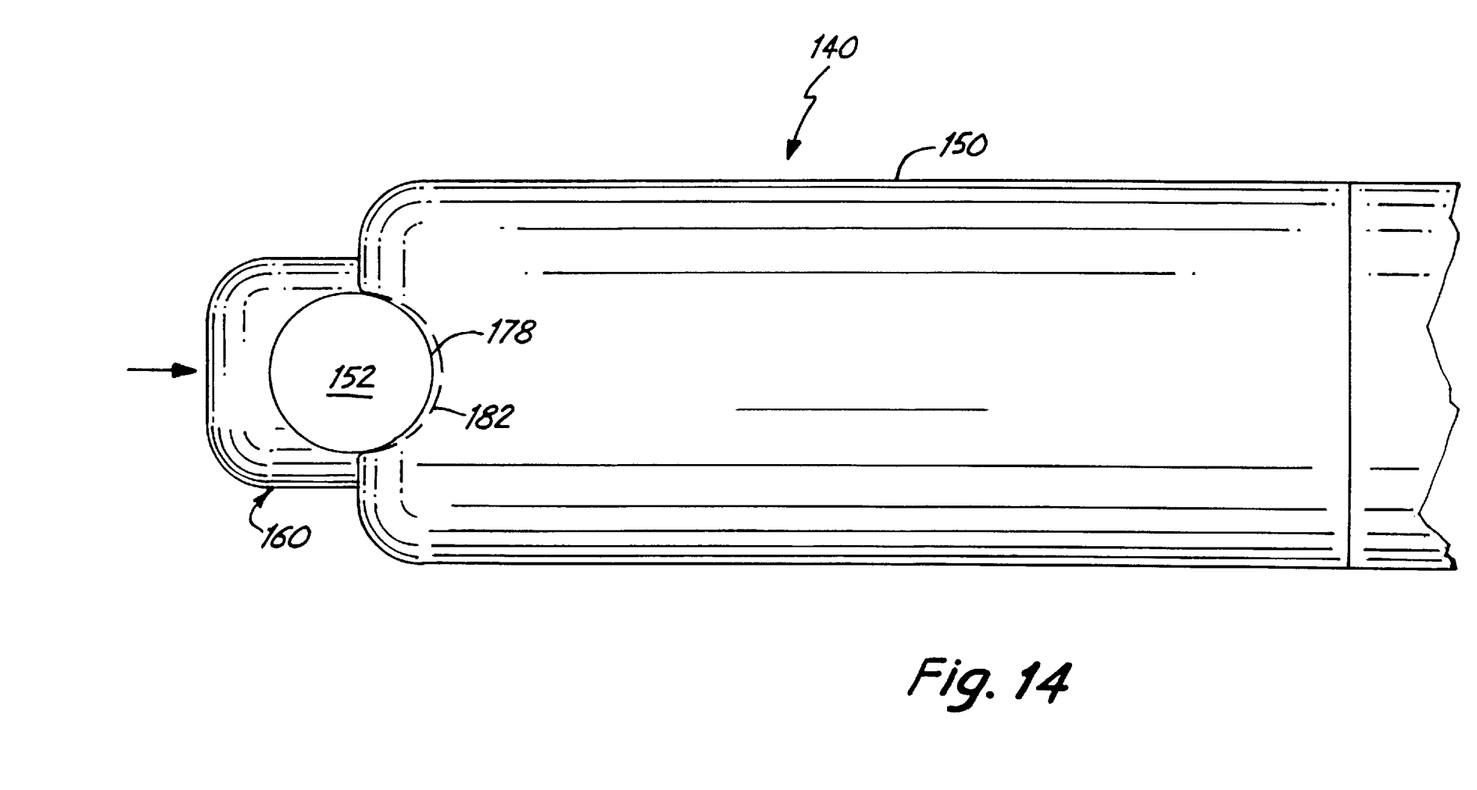
FIG. 14 is a side view of the docking aperture after traveling slightly past the indentation of the housing unit.

When the retractor apparatus 30 is not activated and the adjustable arm 40 is in the relaxed state, the force of the spring 148 substantially aligns a surface of the docking aperture 152 with the semi-circular indentations 178 of the cylindrical housing 150 as illustrated by FIG. 13. However, when the retractor apparatus 30 is activated, the force the spring 148 exerts upon the docking unit 160 is overcome, and the unit 160 is drawn slightly within the cylindrical housing 150. The distance traveled is enough so that a surface of the docking aperture 152 is partially covered by the indentations 178 as illustrated by FIG. 14. Therefore, when the docking pin 142 is inserted through the docking aperture 152, and the retractor apparatus 30 is activated, the indentations 178 of the cylindrical housing 150 come into contact with the docking pin 142, and frictionally lock the docking pin 142 into place.

In one embodiment, a microscope (not shown) is adjustably secured above the proximal end 202 of the tubular retractor 200 for use in surgical procedures, such as direct vision or micro endoscopic discectomy. The microscope has a light fixedly attached to the microscope for viewing a surgical incision under the microscope. The tubular retractor 200 with the microscope is positioned over the surgical incision and the light of the microscope illuminates the surgical incision by transmission of light through the distal end 204 of the tubular retractor 200. Furthermore, the light from the microscope is transmitted along the entire circumference of the distal end 204 of the tubular retractor 200 and illuminates, without shadow formation, an entire portion of the surgical incision.

Figure 6:
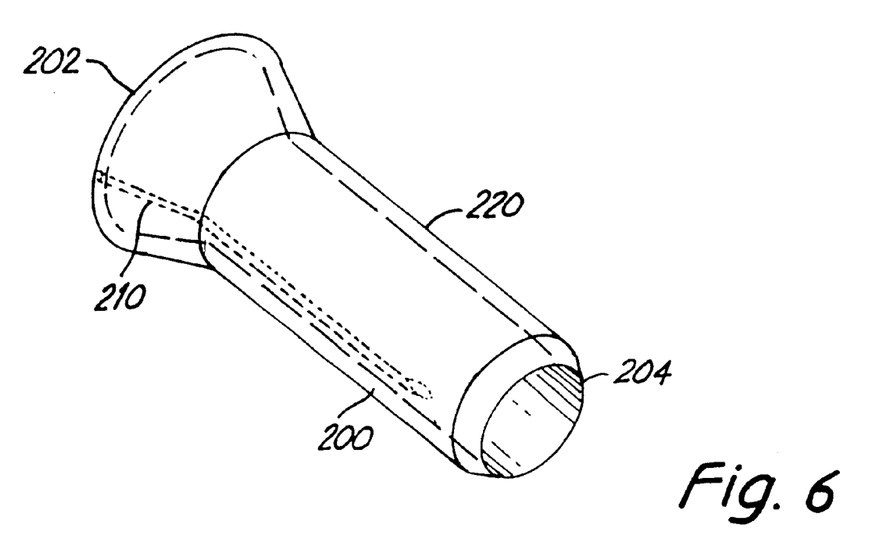
FIG. 6 is a perspective view of a tubular retractor having a fiber optic cable that can be used in the present invention.

In another embodiment, the present invention further includes the use of a fiber optic cable 210 that carries light from a source (not shown) and transmits the light to a distal end 204 of a tubular retractor 200 as illustrated in FIG. 6. In the prior art, the fiber optic cable 210 was positioned within the tubular retractor 200. The transmission of the light into the tubular retractor 200 provided light from a single point. When instrumentation was inserted into the tubular retractor 200 shadows would develop on a side of the instrument opposite of the light to distort the view for the surgeon.

The present embodiment eliminates this problem since the fiber optic cable 210 is positioned within a light carrying case 220 encasing the tubular retractor 200. The fiber optic cable 210 is positioned at least about one-half inch from the distal end 204. When the fiber optic cable 210 is connected to a light source (not shown), light is transmitted through the light carrying case 220 through the distal end 204 and emitted along the entire circumference of the distal end 204. Emission of light along the entire circumference of the distal end 204 eliminates shadows developing on any side of the instrument placed in the tubular retractor 200. Eliminating the fiber optic cable 210 from within the tubular retractor 200 also maximizes working area for any instruments that are placed within the tubular retractor 200.

Figure 7:
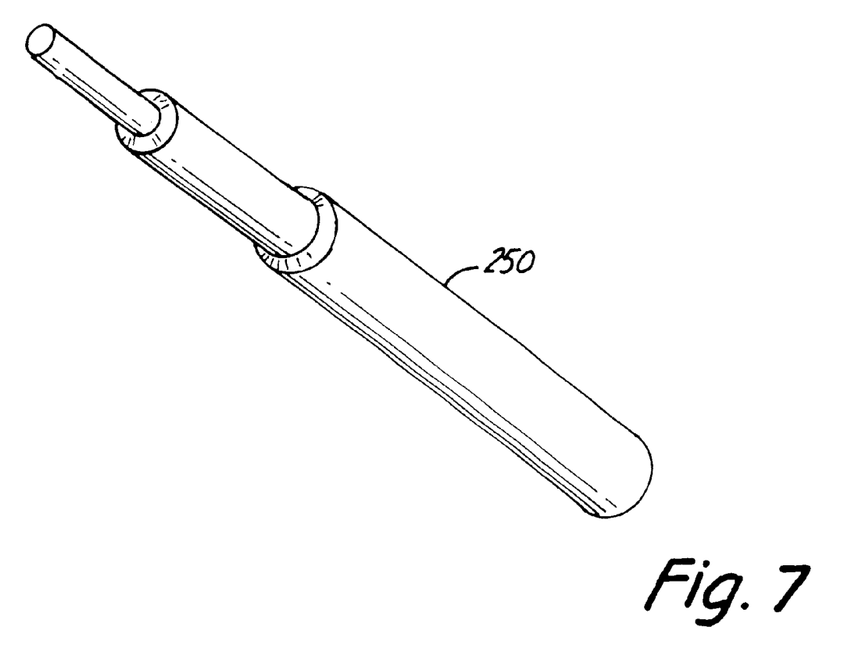
FIG. 7 is a perspective view of a dilator that can be used in the present invention.

By selectively extending the dilator 250 into the incision site, more precise positioning of the tubular retractor 250 can occur.

A set of dilators is used to separate muscle tissue and localize a site for the introduction of dilator retractor.

All though the present invention has been described with reference to preferred embodiments workers skilled in the art would recognize that changes maybe made in form and detail without departing from the spirit and scope of the invention.

What is claimed is:

1. A fastening system for securing a retractor having a docking pin to a retractor support arm, the fastening system comprising:

a housing rotatably attached to the retractor support arm and including a slotted aperture;

a docking unit slidably engaging and being disposed at least partially within the housing, the docking unit including a docking aperture adapted for receiving the docking pin of the retractor; and a travel pin extending from the docking unit and engaging the slotted aperture and thereby defining the amount of travel of the docking unit with respect to the housing.

2. The fastening system of claim 1 wherein the housing and the docking unit frictionally engage the docking pin sufficiently to retain the docking pin within the docking aperture, when the docking unit is drawn within the housing.

3. The fastening system of claim 1 and further including a cable extending through the retractor support arm and cooperatively attached to the docking unit to move the docking unit inwardly and outwardly of the housing.

4. The fastening system of claim 3 and further including a cable tensioning mechanism which tensions and relaxes the cable thereby moving the docking unit with respect to the housing.

5. A fastening mechanism for securing a retractor having a docking pin to a positioning arm, the fastening system comprising:

a housing rotatable attached to the positioning arm and having a slotted aperture;

a docking unit slidably engaging and being at least partially disposed within the housing;

a travel pin extending from the docking unit and engaging the slotted aperture and thereby defining the amount of travel of the docking unit with respect to the housing; and wherein the housing and the docking unit frictionally engage the docking pin of the retractor through movement of the docking unit with respect to the housing thereby retaining the retractor in a selected position.

6. The fastening mechanism of claim 5 wherein the housing is rotatably attached to the positioning arm.

7. The fastening mechanism of claim 5 and further comprising:

a spring for biasing the docking unit in one direction; and a cable attached to the docking unit for pulling the docking unit against the spring.

8. The fastening mechanism of claim 7 wherein the cable is rotatably attached to the docking unit.

9. The fastening mechanism of claim 7 wherein the cable extends through the positioning arm and the housing is rotatably attached to the positioning arm.

10. The fastening system of claim 5 wherein the docking unit includes a docking aperture sufficient in diameter to receive the docking pin.

11. A fastening mechanism for engaging a docking pin attached to a retractor to a positioning arm, the fastening mechanism comprising:

a housing rotatable attached to the positioning arm, the housing having a slotted aperture;

a docking unit slidably engaging and being disposed at least partially within the housing, having a docking pin aperture for receiving the docking pin;

a travel pin extending from the docking unit and engaging the slotted aperture and thereby defining the amount of travel of the docking unit with respect to the housing; and wherein the housing and the docking unit engage the docking pin through movement by the docking unit with respect to the housing to retain the retractor in a selected position when the docking pin is disposed within the docking aperture.

12. The fastening mechanism of claim 1 and further including a positioning arm and wherein the housing is rotatably attached to the positioning arm.

13. The fastening mechanism of claim 12 and further including a cable extending through the positioning arm and cooperatively attached to the docking unit to move the docking unit with respect to the housing.

14. The fastening mechanism of claim 13 and further including a cable tensioning mechanism which tensions and relaxes the cable thereby moving the docking unit with respect to the housing.

* * * * *

UNITED STATES PATENT AND TRADEMARK OFFICE
CERTIFICATE OF CORRECTION

PATENT NO. : 6,663,563 B1 Page 1 of 1
DATED : December 16, 2003
INVENTOR(S) : Todd W. Sharratt

It is certified that error appears in the above-identified patent and that said Letters Patent is hereby corrected as shown below:

Column 7,
Line 25, delete "rotatable" and insert -- rotatably --.

Column 8,
Line 15, delete "rotatable" and insert -- rotatably --.
Line 29, delete "1" and insert -- 11 --.

Signed and Sealed this

Eleventh Day of May, 2004

JON W. DUDAS
*Acting Director of the United States Patent and Trademark Office*